United States Patent [19]

Kurz

[11] Patent Number: 5,146,931
[45] Date of Patent: Sep. 15, 1992

[54] DEVICE TO BE PLACED IN THE UTERUS

[76] Inventor: Karl-Heinz Kurz, Kaiser Wilhelm Ring 22, 4000 Düsseldorf, Fed. Rep. of Germany

[21] Appl. No.: 535,006

[22] Filed: Jun. 8, 1990

Related U.S. Application Data

[63] Continuation of Ser. No. 240,121, Aug. 15, 1988, abandoned.

[51] Int. Cl.⁵ ............................................. A61F 6/14
[52] U.S. Cl. ................................. 128/833; 128/830
[58] Field of Search ............... 128/830, 831, 832, 833, 128/839

[56] References Cited

U.S. PATENT DOCUMENTS

| Re. 30,312 | 6/1980 | Kessel | 128/839 |
|---|---|---|---|
| 3,511,231 | 5/1970 | Robinson | 128/839 |
| 3,533,406 | 10/1970 | Tatum | 128/839 |
| 3,545,439 | 12/1970 | Duncan | 128/832 |
| 3,834,378 | 9/1974 | Lerner et al. | 128/833 |
| 3,898,986 | 8/1975 | Zaffaroni | 128/833 |
| 4,198,966 | 6/1991 | Kaivola | 128/839 |
| 4,578,076 | 3/1986 | Luukkainen | 128/833 |

FOREIGN PATENT DOCUMENTS 350087 1/1990 European Pat. Off. ............ 128/830

Primary Examiner—Robert A. Hafer
Assistant Examiner—Sam Rimell
Attorney, Agent, or Firm—Edmund M. Jaskiewicz

[57] ABSTRACT

Device which is to be placed in the uterus to which certain substances such as metals, metal ions, hormones or therapeutic substances which are to be effective in the uterus for a certain time, can be attached. The device comprises a stem with resilient or flexible arms projecting on either side of the stem near or at one extremity thereof, and the extremity of each of the two arms is bent through an angle greater than 90° so that the extremities point towards the stem. The arms are thus built up of three parts, i.e. a first part and a second part or extension, and a bent piece between them, the three parts of each arm together form an arrow the legs of the arrow being formed by first part and the second part or extension of an arm, the parts being compliantly connected to each other by the bent piece. The direction of the first part near the bent piece points horizontally or upwards.

11 Claims, 3 Drawing Sheets

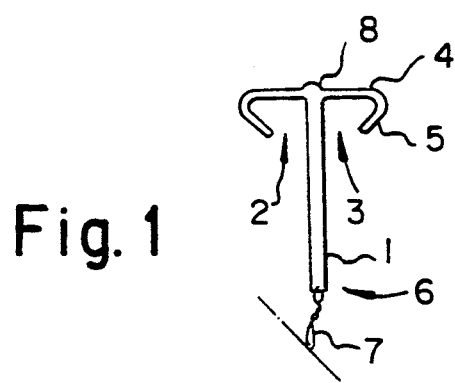
Fig. 1
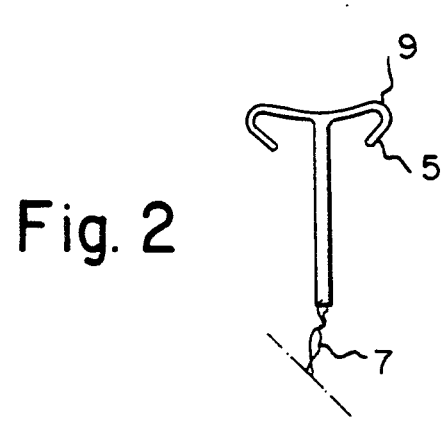
Fig. 2
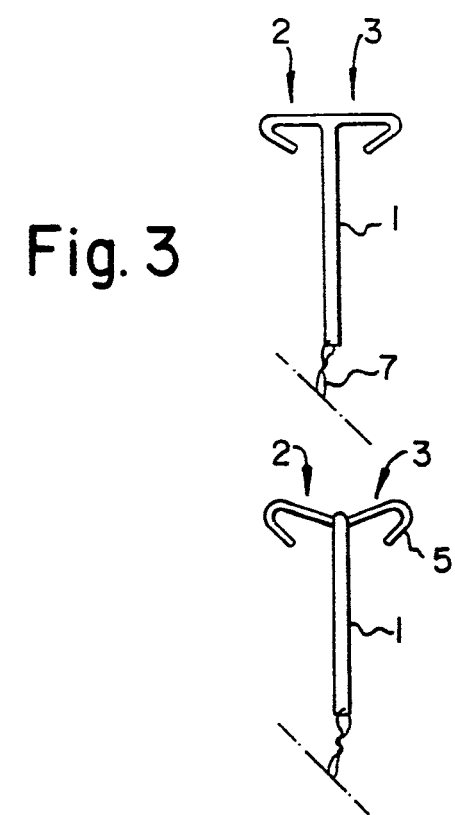
Fig. 3
Fig. 4
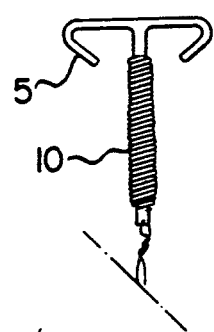
Fig. 5
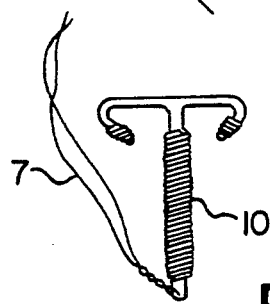
Fig. 6
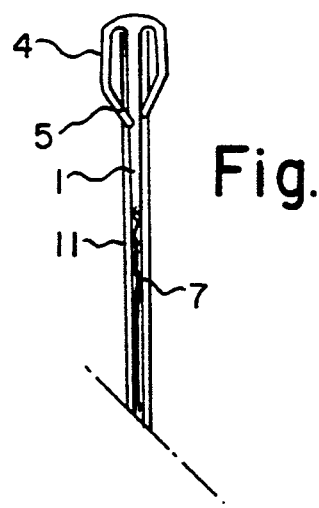
Fig. 7

DEVICE TO BE PLACED IN THE UTERUS

This is a continuation of application U.S. Ser. No. 07/240,121 filed Aug. 18, 1985 now abandoned.

The invention relates to a device which is to be placed in the uterus or uterine cavity and to which or in which certain substances such as metal ions, hormones or therapeutic substances which are to be effective in the uterus for a certain time can be attached, and which device comprises a stem with resilient or flexible arms projecting on either side of the stem near or at one extremity thereof, and the extremity of each of the two arms is bent through an angle greater than 90° so that the extremities point towards the stem and the arms are thus built up of three parts, i.e. a first part and a second part or extension, and a bent piece between them.

Devices which can be placed in the uterus for precluding pregnancy and which are known in medical circles by the name "intrauterine device" or "IUD" are generally known. A device of this type which essentially consists of a "T"-shaped body is described in U.S. Pat. No. 3,533,406. This T-shaped body is to be placed entirely in the uterus. The transverse bar then presses against the fundus or right upper section of the uterus, and the lowermost extremity of the stem is directed towards the orifice of the cervix. It has been found that this device is unsatisfactory in a relatively large number of cases. In a number of cases the device is rejected and in a large number of cases excessive bleeding occurs and such a device is experienced as being painful. Furthermore, in a relatively large number of cases pregnancy is not prevented. The fact that this device is inappropriate is attributed to the extremities of the transverse bars becoming immobilized in the uterine wall, or being at least pushed in, which results in damage to the endometrium or the mucous membrane layer.

U.S. Pat. No. 4,054,131 describes a device likewise having a T-shaped appearance. The extremities of the transverse bar are provided with extensions bent through an angle and directed to the stem. The upper transverse bar is, however, bent towards the outside and downwards and the dimensions and shape of the device are such that the device becomes secured as optimally as possible in the uterine cavity. The transverse bar is bent downwards, and the extremities near the bent piece thus point downwards at an angle, to prevent the device from sliding downwards to the uterine neck or cervix. If, for example, the uterus contracts, the fundus will press on the top of the device and the extremities of the transverse bar will therefore be pushed into the wall of the uterine cavity. To prevent the extremities from penetrating the wall extensions are made at the extremities with the result that the area of pressure is increased. This known device also has the drawback that pain may occur in a relatively large number of cases, the device is rejected and bleeding occurs.

Measurements with measuring instruments developed specifically for this purpose have shown that the uterine cavity in vivo is smaller than assumed hitherto. All of the devices, known to date, which are to be placed in the uterus are shaped such that the best possible anchorage in the uterine cavity is obtained. For this purpose, the dimensions of these known devices are all too large. This is also very probably the reason why pain is felt regularly and why there is often bleeding. This is partially caused by damage to the wall and the tissue at the inner side of the uterine cavity. Another reason may be that the stem extremity of the device projects into the cervix, especially during the period when the uterus contracts greatly.

The invention has as its object a device which can be placed in the uterine cavity and which has or can have dimensions such that the inner wall of the uterine cavity is hardly irritated, if at all.

This object is achieved with a device according to the invention in that the three parts of each arm together form an arrow the legs of which consist of the first part and the second part or extension, these parts being compliantly connected to each other by the bent piece, and the direction of the first part near the bent piece being horizontal or upward. It has been found that these measures make it possible to construct a device which approximately corresponds to the dimensions of the uterine cavity in vivo, or is even smaller, without this device being rejected. The prejudice that a device must be anchored as optimally as possible in the uterine wall was found to be incorrect. Another great advantage of the device according to the invention is that there is hardly any bleeding outside the first period beyond the normally occurring bleeding. The angle enclosed by the first part of the arm and the second part or extension is preferably smaller than 60° so that these extremities can easily slide into the narrowing leading to the fallopian tubes, which is of particular importance when the uterus contracts greatly.

The arrow shape formed by the first part, the second part or extension and the bent part of each arm is preferably a shape between a V and a U. This is particularly important when inserting the device and also when the device is placed in the uterine cavity. With the correct shape the bent extremities of the arms will not easily hook into the wall of the uterine cavity or get stuck. By choosing the position of the extensions of the arms such that they extend approximately parallel to the sidewalls of the uterine cavity it is achieved that the extremities of the arms slide easily along these walls which is particularly important when the uterus contracts. Due to the fact that the device is manufactured of flexible material the two legs of the arrow can moreover easily move towards each other so that the extensions can slide even better along the sidewalls of the uterine cavity without damaging the latter.

In a preferred embodiment of the device according to the invention the point at which the arms are fastened to the stem is reinforced so that the arms resume the original position more easily once the device has been inserted in the uterine cavity. This is because it is important that the arms resume the correct position after insertion.

The thickness of the small arms and the extensions of the small arms is preferably less than 1.5 mm and, when manufactured of plastic material, preferably 1.1 mm or more. It is important that the small arm is so thin in order that the extensions can be sufficiently compliant relative to the first part of the small arms. The small arms should be less thin at the other side because there may otherwise be plastic deformation, and the device will no longer be capable of returning to the original state. In particular, it is very important that the small arms are directed sideways when the device is inserted in the uterine cavity. Another reason why it is important to make the small arms as thin as possible is the fact that bacteria may become settled on the surface of the plastic. Thin round arms have a small surface area. The thickness of the stem of the device is preferably smaller than 2 mm and is preferably of the order of 1.5 mm. In addition, two contradictory interests are to be served, namely the thinner the stem the less is the risk of bacteria; the thicker the stem the more metal, hormones or therapeutic substances can be attached to the stem.

Measurements on the uterine cavity in vivo have shown that the width of each device ought to be adapted to the dimensions of a uterine cavity. It has generally been found, however, that it is sufficient, at least for European women, to have a limited number of different dimensions of the device. In principle, three standard dimensions for the maximum width of the devices are sufficient, i.e. 20 mm, 24 mm and 28 mm. This width is coupled with a maximum length of the stem of 28 mm, 30 mm and 32 mm, respectively. This length of the stem is more or less the maximum acceptable length because the lower end of the stem must not reach the region of the internal os which is rich in nerves. For this purpose account is to be taken of the contraction of the uterus and the flexion which most uteri have at the transition of the uterine cavity into the cervix.

It has been found in practice that, when a limited number of standard dimensions of the device according to the invention is taken as a starting point and the uterine cavity was measured beforehand, the accompanying symptoms such as excessive bleeding, pain and rejection of the device can be prevented virtually entirely when the correct dimersion of the device is used for a certain measured width of a uterine cavity.

The invention will be illustrated in detail by reference to the drawing, in which:

FIGS. 1, 2, 3 and 4 show four different possible embodiments of the device according to the invention;

FIGS. 5 and 6 show a device as represented in FIG. 1, provided with copper wire;

FIG. 7 shows the device according to FIG. 1 in which the small arms are folded downwards;

Figure 8:
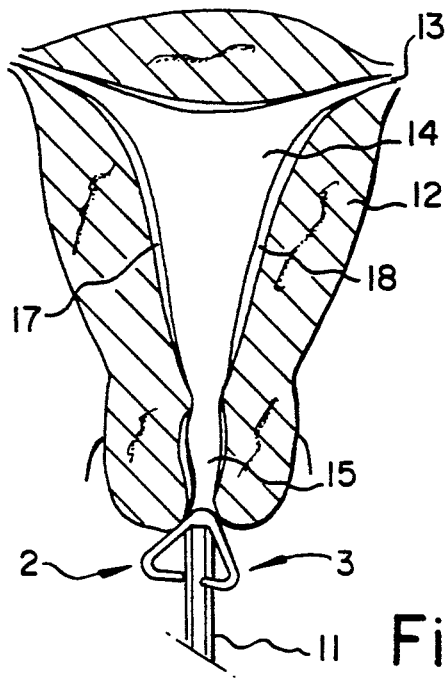
FIGS. 8, 9 and 10 show the uterine cavity in cross-section with the device according to the invention during insertion into the uterine cavity.

FIGS. 1, 2, 3 and 4 show four different possible embodiments of a device according to the invention. Each device consists of a stem 1 with two arms 2, 3 projecting at either side at the upper extremity. The device according to FIG. 1 shows two arms 2, 3 consisting of a first part 4 which is straight and is then bent through an angle of the order of magnitude of 35°, and thereafter a second part or extension 5 which points in the direction of the stem 1 and has a length of approximately 6 mm. The hook over which the extremities of the arms 2,3 are bent is circular and in this case has an inner diameter of 2 mm and an outer diameter of approximately 4 mm. The thickness of the small arms and the bent extensions is approximately 1. mm. The thickness of the stem is approximately 1.5 mm round. The small arms as well as the stem are circular. A small hole 6 through which a small wire 7 is fitted is attached near the lower end of the stem 1. The device is provided with a thickening 8 present at the upper side of the device at the point where the stem 1 is fastened to the arms 2,3. The angle which the straight part 4 of each of the arms 2,3 forms with the stem 1 is in this case 90°.

FIG. 2 shows a device which also consists of a stem 1 with a small hole 6 through which a small wire 7 extends near the lower side. The first part 9 of the arms 2,3 is in this case not straight but slightly bent upwards. FIG. 3 shows a device according to the invention in which the angle through which the extremities of the two arms 2, 3 are bent is sharp and has approximately a V shape. FIG. 4 shows a device according to the invention in which the angle between the first straight part 5 of the arms 2, 3 and the stem is greater than 90° and the arms thus extend obliquely upwards relative to the stem 1.

FIG. 5 shows a device according to the invention such as is represented in FIG. 1 in which a wire 10 is wound round the stem. In this case, this is a copper wire used as a means for introducing copper ions into the uterus during a lengthy period. FIG. 6 furthermore shows the possibility of fitting wires not only to the stem but also to the bent parts or extensions 5 of the device; as a result copper ions will be present even at the sidewall of the uterine cavity. In the same manner other therapeutic or hormonal agents can be attached at the outer surface of the stem 1 and/or arm parts 4, 5. For this purpose it should be possible to attach wires at the outer surface of the device which are impregnated with the desired agent. FIG. 7 shows the downwardly folded state of the device according to the invention; this is the position of the arms when these are pushed into the uterine cervix by means of a small tube 11.

Figure 9:
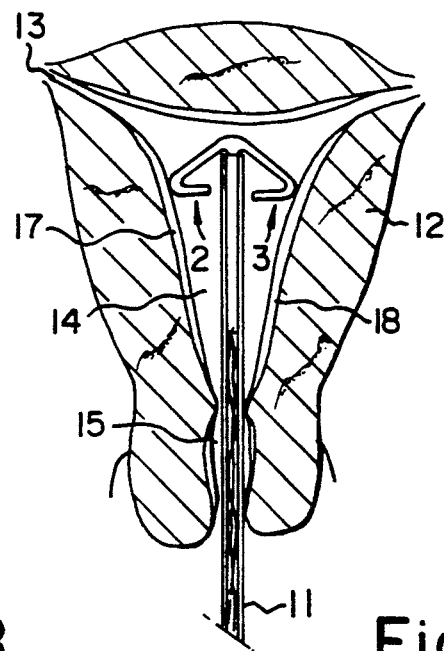
Figure 10:
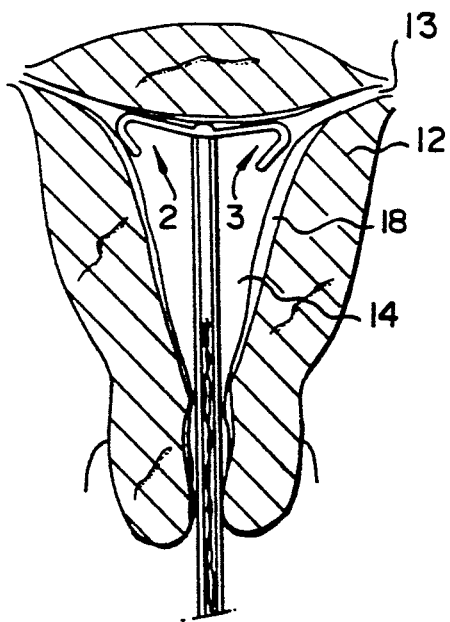

FIGS. 8, 9 and 10 show a cross-section of a uterus 12 with the fallopian tubes 13, the uterine cavity 14 and the cervix 15. FIG. 8 shows the device according to the invention at the instant at which this is pushed into the cervix 15 by means of the small tube 11. The arms 2, 3 will be bent downwards away after which the small tube is pushed with the device through the cervix 15 to arrive, subsequently, in the uterine cavity. When a device having the correct dimensions is used the arms 2, 3 will subsequently have sufficient space near the upper side of the uterine cavity for springing back into the original state sideways and upwards. When the small tube is then taken out of the uterine cavity again the device will remain in the uterine cavity because the arms 2, 3 which are extended sideways will press against the sidewalls of the uterine cavity and as a result of this will remain clamped between the sidewalls 17, 18 of the uterine cavity.

Figure 11:
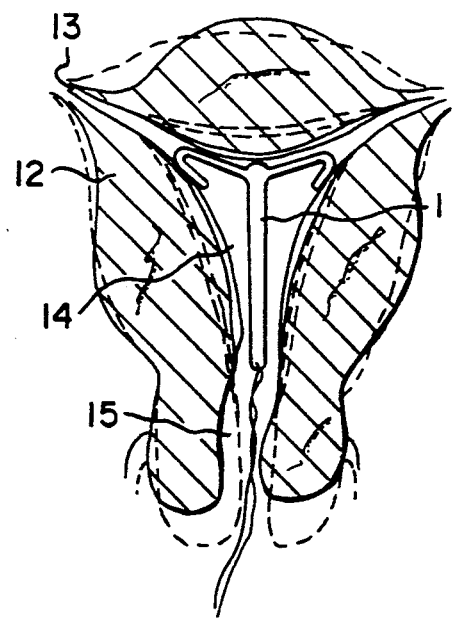
FIG. 11 shows the uterus in cross-section in two positions with a device according to the invention.

FIG. 11 shows the uterus 12 in the state in which it is contracted; the state of the uterus at the instant at which it is relaxed is at the same time shown in dashed lines. In the state in which the uterus is contracted the arms 2, 3 of the device will be somewhat bent and, such as represented here, slightly bent upwards and the bent parts 5 of the arms 2, 3 will possibly be pushed slightly inwards, i.e. the extension 5 towards the first parts 4 of the arms. In the relaxed state of the uterus this device, as represented in FIG. 11, will resume the position as shown in FIG. 10. The device can be easily removed at a certain desired instant by means of the small wire 7.

Figure 12:
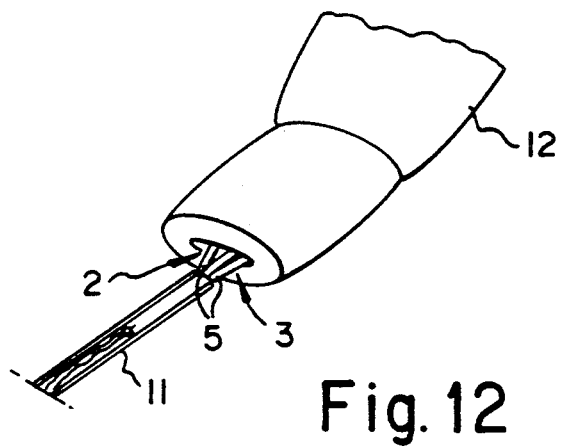
FIG. 12 shows a view of the uterus near the cervix.

FIG. 12 shows a view of a uterus and in particular that section which contains the cervix. A small section of the device and also the extensions 5 of the arms 2, 3 together with the small tube 11 for introducing the device into the uterine cavity are still inserted in the cervical os which is somewhat slit-shaped.

Figure 13:
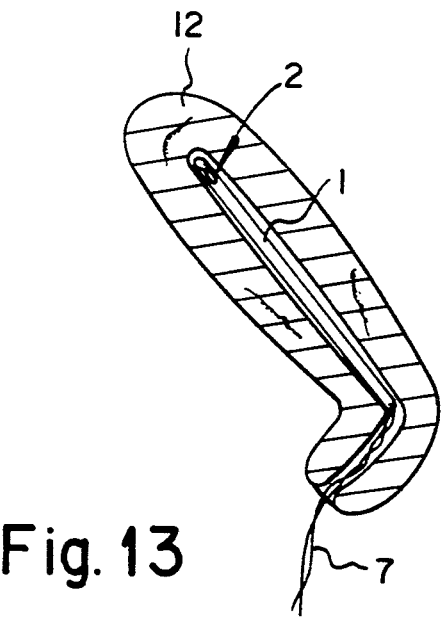
FIG. 13 shows a cross-section through a uterus perpendicular to the section as represented in FIGS. 8, 9 and 10.
Figure 14:
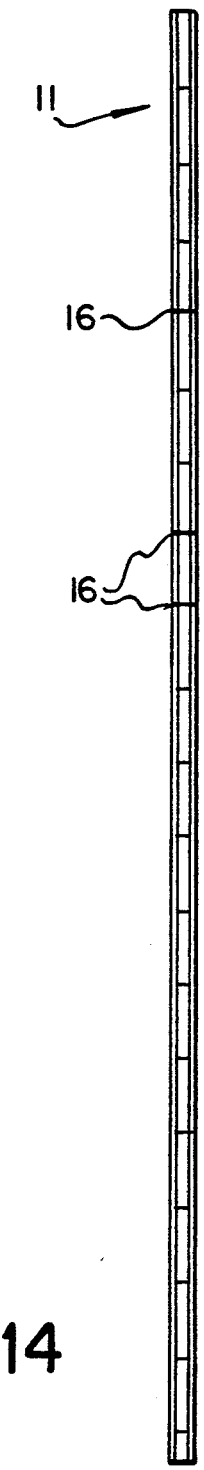
FIG. 14 shows a view of a small bar for insertion of a device according to the invention.

FIG. 13 shows a cross-section through the uterus such as represented in FIGS. 8, 9 and 10 in a direction perpendicular to the section represented in those figures. As is often the case, the uterus shows flexion are the device must not be so long that the lowermost end reaches the section of the inner uterine cavity which is rich in nerves. FIG. 14 shows a further small tube with which the device can be inserted in the uterine cavity and to which certain indicators can be attached such as, for example, a tape measure with a number of coloured rings 16.

The device according to the invention has great advantages over the devices known to date, in that the device according to the invention is adapted to the shape of the uterine cavity and thereby takes account of the size of the uterine cavity in vivo because the latter may be smaller, as a result of contraction, than measured after it has been removed from the body. The device according to the invention will easily remain within the cavity, even when the uterus contracts, without the device being pressed against the walls of the cavity in a manner such that parts of the device are pushed into the wall. Even the layer of mucous membrane in the uterine cavity is hardly damaged by the device according to the invention. As a result of the fact that the device is small in size, and therefore lightweight, the weight will hardly exert forces on the device which could be a cause for the device to be rejected or at least to fall out of the cavity. A further advantage of the small size is that the outer surface area of the device is very small with the result that fewer bacteria may be present on the device. Specifically, it is generally known that some bacteria such as Staphylococcus epididermidis can multiply on the surface of plastics. Only in the first month after insertion of the device into the uterus may there be somewhat more bleeding than normal, because the layer of mucous membrane and the muscular tissue of the uterine cavity may be slightly irritated by the insertion.

Since it is possible at present to determine and measure very accurately the inner dimensions of the uterine cavity in a living individual the size of the uterine cavity can be taken into account and the appropriate size of the device determined beforehand. It has been found that at least in Europe three standard dimensions are sufficient, that is to say a length of the stem of 28 mm, 30 mm and 32 mm with an appropriate maximum width of the device of 20 mm, 24 mm and 28 mm, respectively. Two further dimensions may optionally be added to this, that is to say: stem length 26 mm and 34 mm with the appropriate dimensions for the maximum width of 16 mm and 32 mm, respectively.

I claim:

1. Device which is to be placed in the uterus and to which certain substances particularly metals, metal ions, hormones and therapeutic substances which are to be effective in the uterus for a certain time, can be attached, and comprising a stem having two resilient arms projecting on opposed sides of the stem at one extremity thereof, the extremity of each of the two arms is bent through an angle greater than 90° so that the extremities point towards the stem and the arms are thus built up of three parts, comprising a first part attached to the stem and a second extension part having a free end and a bent piece having an inner radius of curvature between them, the three parts of each arm together define an arrow comprising the first part and the second part of a said arm, the parts of a said arm being compliantly connected to each other by the bent piece, and the first part of each said arm being straight and projecting between either a horizontal position or slightly obliquely upward position.

2. Device according to claim 1, characterized in that the angle enclosed by the first part and the second part of each arm is smaller than 60°.

3. Device according to one of claims 1 or 2, characterized in that the shape of the arms near the bent piece is between the shape of a V and a U.

4. Device according to claim 1 wherein the device is provided with a thickening near the place where the stem and the two arms are connected to each other.

5. Device according to claim 1 wherein the stem thickness is smaller than 2 mm.

6. Device according to claim 1 wherein the thickness of the arms is smaller than 1.5 mm.

7. Device according to claim 1 wherein a maximum width of the device of 24 mm is associated with a maximum stem length of 30 mm.

8. Device according to claim 1 wherein standard models have different dimensions comprising stem lengths of 28 mm, 30 mm and 32 mm with maximum widths of 20 mm, 24 mm and 28 mm respectively.

9. Device according to claim 1 wherein the cross-section of the stem is round.

10. Device according to claim 1 wherein the cross-section of the small arms is round.

11. Device according to claim 1 wherein said straight first parts of said arms each define an angle of 70°-90° with a line vertically extended from said stem.

* * * * *